United States Patent

Ishida et al.

(10) Patent No.: US 8,980,060 B2
(45) Date of Patent: Mar. 17, 2015

(54) BIOMASS HYDROTHERMAL DECOMPOSITION APPARATUS, METHOD THEREOF, AND ORGANIC MATERIAL PRODUCTION SYSTEM USING BIOMASS MATERIAL

(75) Inventors: Isao Ishida, Hyogo (JP); Seiichi Terakura, Hyogo (JP); Hideo Suzuki, Hyogo (JP); Seiji Kobayashi, Hyogo (JP)

(73) Assignee: Mitsubishi Heavy Industries Mechatronics Systems, Ltd., Kobe (JP)

( * ) Notice: Subject to any disclaimer, the term of this patent is extended or adjusted under 35 U.S.C. 154(b) by 0 days.

(21) Appl. No.: 12/443,515

(22) PCT Filed: Sep. 19, 2008

(86) PCT No.: PCT/JP2008/067038
§ 371 (c)(1),
(2), (4) Date: Mar. 30, 2009

(87) PCT Pub. No.: WO2009/096060
PCT Pub. Date: Aug. 6, 2009

(65) Prior Publication Data
US 2010/0184176 A1    Jul. 22, 2010

(30) Foreign Application Priority Data

Feb. 1, 2008   (JP) ................. 2008-023188

(51) Int. Cl.
*B02C 11/08*   (2006.01)
*B02C 21/00*   (2006.01)
(Continued)

(52) U.S. Cl.
CPC .............. *B01D 11/0226* (2013.01); *B09B 3/00* (2013.01); *B09B 3/0083* (2013.01);
(Continued)

(58) Field of Classification Search
CPC ..... B01D 11/0226; B09B 3/00; B09B 3/0083
USPC .......... 435/290.1, 290.2, 290.4, 291.1, 291.7; 71/11, 14, 15; 162/1, 223, 234, 244, 162/248, 250; 241/20, 21, 28, 38
See application file for complete search history.

(56) References Cited

U.S. PATENT DOCUMENTS 3,833,461 A * 9/1974 Woodruff ................... 162/19
3,985,728 A   10/1976 Lin
(Continued)

FOREIGN PATENT DOCUMENTS

CA   2 448 862 A1   9/2002
CA   2654306 A1   8/2009
(Continued)

OTHER PUBLICATIONS

English language translation of WO 9618590.*
(Continued)

*Primary Examiner* — Nathan Bowers
(74) *Attorney, Agent, or Firm* — Westerman, Hattori, Daniels & Adrian, LLP

(57) ABSTRACT

A biomass hydrothermal decomposition apparatus includes, a biomass feeder (31) that feeds biomass material (11) under normal pressure to under increased pressure, a hydrothermal decomposition device (42A) that allows the fed biomass material (11) to be gradually moved inside a device main body (42A) from either end thereof in a consolidated condition, and also allows hot compressed water (15) to be fed from an other end of a feed section for the biomass material into the main body (42A), so as to cause the biomass material (11) and the hot compressed water (15) to countercurrently contact with each other and undergo hydrothermal decomposition, and that elutes a lignin component and a hemicellulose component into the hot compressed water, so as to separate the lignin component and the hemicellulose component from the biomass material (11); and a biomass discharger (51) that discharges, from the side where the hot compressed water is fed into the device main body, a biomass solid residue (17) under increased pressure to under normal pressure.

15 Claims, 10 Drawing Sheets

(51) Int. Cl.
*D21C 7/00* (2006.01)
*B01D 11/02* (2006.01)
*B09B 3/00* (2006.01)
*C08B 37/00* (2006.01)
*C08H 7/00* (2011.01)
*C10L 5/44* (2006.01)
*C10L 9/08* (2006.01)
*C12P 7/10* (2006.01)
*C12M 1/00* (2006.01)
*C12M 1/33* (2006.01)

(52) U.S. Cl.
CPC .............. *C08B 37/0057* (2013.01); *C08H 6/00* (2013.01); *C10L 5/44* (2013.01); *C10L 9/086* (2013.01); *C12P 7/10* (2013.01); *C12M 21/12* (2013.01); *C12M 45/02* (2013.01); *C12M 45/20* (2013.01); *C12P 2201/00* (2013.01); *Y02E 50/10* (2013.01); *Y02E 50/16* (2013.01); *Y02E 50/17* (2013.01); *Y02E 50/30* (2013.01)
USPC ............... 162/233; 162/234; 162/223; 162/1; 162/244; 162/248; 241/20; 241/21; 241/28; 241/38

(56) References Cited

U.S. PATENT DOCUMENTS

| | | | |
|---|---|---|---|
| 4,152,197 A | | 5/1979 | Lindahl et al. |
| 4,443,540 A | * | 4/1984 | Chervan et al. ............... 435/68.1 |
| 4,746,401 A | | 5/1988 | Roberts et al. |
| 5,348,871 A | | 9/1994 | Scott et al. |
| 5,466,108 A | * | 11/1995 | Piroska .......................... 414/218 |
| 5,846,787 A | * | 12/1998 | Ladisch et al. .................. 435/99 |
| 6,022,419 A | | 2/2000 | Torget et al. |
| 6,039,774 A | * | 3/2000 | McMullen et al. ........ 48/102 A |
| 6,419,788 B1 | | 7/2002 | Wingerson |
| 2002/0151034 A1 | | 10/2002 | Zhang et al. |
| 2006/0280663 A1 | * | 12/2006 | Osato et al. ................... 422/226 |
| 2007/0231869 A1 | | 10/2007 | Holmgren et al. |
| 2007/0259412 A1 | | 11/2007 | Belanger et al. |
| 2008/0028675 A1 | * | 2/2008 | Clifford et al. .................. 44/605 |
| 2008/0032344 A1 | * | 2/2008 | Fallavollita ...................... 435/72 |
| 2008/0044891 A1 | | 2/2008 | Kinley et al. |
| 2008/0299628 A1 | | 12/2008 | Hallberg et al. |
| 2009/0077729 A1 | * | 3/2009 | McLeod ........................... 4/300 |
| 2009/0283397 A1 | * | 11/2009 | Kato et al. ..................... 202/208 |
| 2010/0184176 A1 | | 7/2010 | Ishida et al. |
| 2010/0285574 A1 | | 11/2010 | Genta et al. |
| 2011/0003348 A1 | | 1/2011 | Genta et al. |
| 2011/0314726 A1 | | 12/2011 | Jameel et al. |

FOREIGN PATENT DOCUMENTS

| | | | |
|---|---|---|---|
| CA | 2666152 A1 | 4/2010 | |
| EP | 0 098 490 A2 | 1/1984 | |
| JP | 9-507386 A | 7/1997 | |
| JP | 11-172262 A | 6/1999 | |
| JP | 11-506934 A | 6/1999 | |
| JP | 3042076 B2 | 5/2000 | |
| JP | 2002-59118 A | 2/2002 | |
| JP | 2002-105466 A | 4/2002 | |
| JP | 2003-219900 A | 8/2003 | |
| JP | 2005-027541 A | 2/2005 | |
| JP | 2005-168335 A | 6/2005 | |
| JP | 2005-205252 A | 8/2005 | |
| JP | 2005-229821 A | 9/2005 | |
| JP | 2005-534343 A | 11/2005 | |
| JP | 2006-036977 A | 2/2006 | |
| JP | 2006-136263 A | 6/2006 | |
| JP | 2006-223152 A | 8/2006 | |
| JP | 2006-289164 A | 10/2006 | |
| JP | 2007-112880 A | 5/2007 | |
| JP | 2007-202560 A | 8/2007 | |
| JP | 2007-301472 A | 11/2007 | |
| JP | 2008-054608 A | 3/2008 | |
| JP | 2008-104452 A | 5/2008 | |
| JP | 2008-278825 A | 11/2008 | |
| JP | 2009-183153 A | 8/2009 | |
| JP | 2009-183154 A | 8/2009 | |
| JP | 2009-183805 A | 8/2009 | |
| JP | 2010-17084 A | 1/2010 | |
| WO | 84/03304 A1 | 8/1984 | |
| WO | 95/17517 A1 | 6/1995 | |
| WO | WO 9618590 A1 | * | 7/1996 |
| WO | 96/40970 A1 | 12/1996 | |
| WO | 2004-037973 A2 | 5/2004 | |
| WO | 2009/096062 A1 | 8/2009 | |
| WO | 2009/124240 A1 | 10/2009 | |
| WO | 2010/038302 A1 | 4/2010 | |

OTHER PUBLICATIONS

English translation of Greeb WO 96/18590, Jun. 1996.*
English translation of Nakagame (JP 2007301472).*
International Search Report of PCT/JP2008/067038, mailing date of Nov. 18, 2008.
Japanese Office Action dated Oct. 23, 2012, issued in Japanese Patent Application No. 2009-245963, with English translation (5 pages).
Japanese Office Action dated Oct. 23, 2012, issued in corresponding Japanese Patent Application No. 2009-252201, with English translation (9 pages).
Canadian Office Action dated Oct. 3, 2012, issued in corresponding Canadian Patent Application No. 2,660,990, (3 pages).
Canadian Office Action dated Feb. 16, 2012, issued in corresponding Canadian Patent Application No. 2,660,990.
Canadian Notice of Allowance dated Aug. 22, 2013, issued in corresponding Canadian Patent Application No. 2,713,529.
Indonesian Notice of Allowance dated Jun. 26, 2013, issued in corresponding Indonesian Patent Application No. W-00200902415, w/English translation.
U.S. Office Action dated Aug. 19, 2013 issued in U.S. Appl. No. 13/578,116.
Arroyo-Lopez, F.N. et al., "Effects of temperature, pH and sugar concentration on the growth parameters of *Saccharomyces cerevisiae, S. kudriavzevii* and their interspecific hybrid", International Journal of Food Microbiology, vol. 131, pp. 120-127 (2009).
Turton, L.J. et al., "Effect of Glucose Concentration in the Growth Medium Upon Neutral and Acidic Fermentation End-products of *Clostridium bifermentans, Clostridium sporogenes* and *Peptostreptococcus Anaerobius*", J. Med. Microbiol., vol. 16, pp. 61-67 (1983).
Dien, B.S. et al., "Fermentation of hexose and pentose sugars using a novel ethanologenic *Escherichia coli* strain", Enzyme and Microbial Technology, vol. 23, pp. 366-371 (1998).
U.S. Office Action dated Oct. 3, 2013 issued in U.S. Appl. No. 13/782,545.
Canadian Notice of Allowance dated Aug. 22, 2013, issued in Canadian Patent Application No. 2666152.
U.S. Office Action dated Oct. 28, 2013, issued in U.S. Appl. No. 12/443,515.
U.S. Office Action dated Oct. 7, 2013, issued in U.S. Appl. No. 13/700,753.
U.S. Restriction/Election dated Aug. 22, 2013, issued in U.S. Appl. No. 13/700,753.
U.S. Non-Final Office Action dated Dec. 17, 2013, issued in U.S. Appl. No. 13/203,929 (23 pages).
U.S. Non-Final Office Action dated Dec. 16, 2013, issued in U.S. Appl. No. 13/132,034 (29 pages).
U.S. Non-Final Office Action dated Jan. 30, 2014, issued in U.S. Appl. No. 13/578,116 (22 pages).
U.S. Non-Final Office Action dated Jan. 30, 2014 issued in U.S. Appl. No. 12/438,792 (39 pages).
Indonesian Notice of Allowance dated Nov. 15, 2013, issued in Indonesian Patent Application No. W-00201002623, w/English translation, (5 pages).
Canadian Office Action dated Nov. 8, 2013, issued in Canadian Patent Application No. 2,801,383 (2 pages).
Canadian Notice of Allowance dated Jan. 13, 2014, issued in Canadian Patent Application No. 2,744,522 (1 page).
Gregg, D. et al., "Bioconversion of Lignocellulosic Residue to Ethanol: Process Flowsheet Development", Biomass and Bioenergy, 1995, vol. 9, No. 1-5, pp. 287-302, Cited in U.S. Office Action dated Dec. 17, 2013.

(56) References Cited

OTHER PUBLICATIONS

Genta, "NEDO ni yoru Biomass Energy to Ko Koritsu Tenkan Gijutsu Kaihatsu 1), Suinetsu Bunkaiho to Koso Bunkaiho wo Kumiawaseta Nogyo Zansa to no Cellulose-kei Biomass no Tei Cost Toka Gijutsu no Kaihatsu" Clean Energy, 2010, pp. 11-15.
Canadian Office Action dated Mar. 31, 2014, issued in Canadian Patent Application No. 2,750,753 (3 pages) (corresponding to U.S. Appl. No. 13/203,929).
U.S. Final Office Action dated May 22, 2014, issued in U.S. Appl. No. 13/700,753 (40 pages).
U.S. Final Office Action dated Jun. 3, 2014, issued in U.S. Appl. No. 13/203,929 (22 pages).
Kumagai Satoshi et al. "Fractionation and Saccharification of Cellulose and Hemicellulose in Rice Hull by Hot-Compressed-Water Treatment with Two-Step Heating", Journal of the Japan Institute of Energy, Dec. 1, 2004, vol. 83, pp. 776-781, Cited in Notice of Acceptance dated Mar. 4, 2014, issued in Japanese Patent Application No. 2009-252201.
US Final Office Action dated Feb. 13, 2014, issued in U.S. Appl. No. 12/865,273 (26 pages).
Liu, Chaogang, et al., "Continuous Fermentation of Hemicellulose Sugars and Cellulose to Ethanol", International Symposia on Alcohol Fuels, (2005), pp. 1-28 (cited in U.S. Final Office Action dated Feb. 13, 2014, issued in U.S. Appl. No. 12/865,273).
U.S. Non-Final Office Action issued Mar. 10, 2014, in U.S. Appl. No. 13/782,545 (27 pages).
Decision of a Patent Grant dated Mar. 4, 2014, issued in JP2009-252201 (corresponding to U.S. Appl. No. 12/443,515), w/English translation (4 pages).
Decision of a Patent Grant dated Mar. 4, 2014, issued in JP2009-245963 (corresponding to U.S. Appl. No. 12/438,972) w/English translation (4 pages).
Australian Notice of Acceptance dated Mar. 17, 2014, issued in Australian patent application No. 2011355013 (corresponding to U.S. Appl. No. 13/578,116, (2 pages).
International Search Report of PCT/JP2008/067038, date of mailing date Nov. 11, 2008.
Biomass Ethanol Up to 80% sachharification is possible; Nikkei Biotechnology & Business; Sep. 2002.
Biomass-Extensive Use of Bioresources (2) Saccharification of boimass; Agricultural and Biological Chemistry Series.
Anneli Nilsson, "Control of fermentation of lignocellulosic hydrolysates", Department of Chemical Engineering II, Lund University, Sweden (6 pages), 1999.
Japanese Office Action dated Dec. 15, 2009, issued in Japanese Patent Application No. 2008-023185 (corresponding to U.S. Appl. No. 12/865,273) w/English translation.
Canadian Office Action dated Mar. 7, 2012, issued in Canadian Patent Application No. 2,654,306 (corresponding to U.S. Appl. No. 12/348,792) (3 pages).
International Search Report of PCT/JP2008/067040 (corresponding to U.S. Appl. No. 12/348,792), dated Dec. 16, 2008.
US Office Action dated Oct. 19, 2010, issued in U.S. Appl. No. 12/438,792.
US Office Action dated Mar. 7, 2011, issued in U.S. Appl. No. 12/438,792.
US Advisory Action dated Jun. 16, 2011, issued in U.S. Appl. No. 12/438,792.
Examiner's Answer to Appeal Brief dated Nov. 4, 2011, issued in U.S. Appl. No. 12/438,792.
International Search Report of PCT/JP2008/067039 (corresponding to U.S. Appl. No. 12/865,273), Mailing Date of Dec. 16, 2008.
Canadian Office Action dated Sep. 20, 2012, issued in Canadian Patent Application No. 2,654,306 (corresponding to U.S. Appl. No. 12/348,792).
Canadian Office Action dated Feb. 25, 2013, issued in Canadian Patent Application No. 2,654,306 (corresponding to U.S. Appl. No. 12/348,792).
Canadian Office Action dated Apr. 10, 2012, issued in Canadian Patent Application No. 2,713,529 (corresponding to U.S. Appl. No. 12/865,273).
Canadian Office Action dated Jan. 15, 2013, issued in Canadian Patent Application No. 2,713,529 (corresponding to U.S. Appl. No. 12/865,273).
Canadian Notice of Allowance dated Jun. 26, 2013, issued in corresponding Canadian Patent Application No. 2,654,306 (1 page).
Canadian Notice of Allowance dated Jul. 2, 2013, issued in Canadian Patent Application No. 2,660,990 (corresponding to U.S. Appl. No. 12/348,792) (1 page).
US Office Action dated Apr. 27, 2012, issued in U.S. Appl. No. 12/865,273.
Ando et al. "Decomposition behavior of plant biomass in hot-compressed water", Industrial and Engineering Chemistry Research, 2000; vol. 39, pp. 3688-3693.
Mosier et al. "Features of promising technologies for pretreatment of lignocellulosic biomass", Bioresource Technology 2005; vol. 96, pp. 673-686.
US Office Action dated Jun. 25, 2012, issued in U.S. Appl. No. 12/865,273.
Olsson et al., "Fermentation of lignocellulosic hydrosylates for ethanol production", Enzyme and Microbial Technology, 1996, vol. 18, pp. 312-331.
Garrote et al., "Hydrothermal processing of lignocellulosic materials", Holz als Roh-und Werkstoff. 1999; vol. 57, pp. 191-202.
US Office Action dated Dec. 4, 2012, issued in U.S. Appl. No. 12/865,273.
US Office Action dated Jun. 4, 2013, issued in U.S. Appl. No. 12/865,273.
English language machine translation of WO 9618590; cited in US Office Action dated Mar. 29, 2011, issued in U.S. Appl. No. 12/865,273.
U.S. Final Office Action dated Jul. 3, 2014, issued in U.S. Appl. No. 13/578,116 (17 pages).
U.S. Final Office Action dated Aug. 18, 2014, issued in U.S. Appl. No. 13/132,034 (30 pages).
U.S. Final Office Action dated Jun. 13, 2014, issued in U.S. Appl. No. 12/438,792 (26 pages).
U.S. Non-Final Office Action dated Aug. 27, 2014, issued in U.S. Appl. No. 13/132,040 (53 pages).
Genda, M. et al., "Suinetsu Bunkaiho to Koso Bunkaiho o Kumiawaseta Nogyo Zansa to no Cellulose Biomass no Tei Cost Toka Gijutsu no Kaihatsu", Heisei 21 Nendo Biomass Energy Kanren Jigyo Seika Hokokukai, Feb. 11, 2010, pp. 55-69, URL, http://www.nedo.go.jp/events/report/FF_00003.html, Cited in JP Office Action dated Oct. 14, 2014.
Lehrburger, E. "Developing biorefineries to produce energy, ethanol and other industrial products", PureVision Technology, Inc., Alternative Energy Conference, Mar. 3, 2005, pp. 1-26, Cited in U.S. Office Action dated Nov. 6, 2014.
U.S. Office Action dated Sep. 30, 2014, issued in related U.S. Appl. No. 13/782,545 (43 pages).
U.S. Office Action dated Nov. 6, 2014, issued in related U.S. Appl. No. 12/865,273 (27 pages).
Office Action dated Oct. 14, 2014, issued in JP 2010-154233 (corresponds to U.S. Appl. No. 13/700,753), with English Translation (7 pages).
U.S. Office Action dated Dec. 5, 2014, issued in U.S. Appl. No. 13/121,969.
Canadian Notice of Allowance dated Dec. 5, 2014, issued in Canadian Patent Application No. 2750754 (corresponds to U.S. Appl. No. 13/203,848).
Indonesian Office Action dated Oct. 29, 2014, issued in Indonesian Patent Application No. W00201103522 (corresponds to U.S. Appl. No. 13/700,753), w/English translation.
U.S. Office Action dated Dec. 26, 2014, issued in U.S. Appl. No. 13/132,040.

\* cited by examiner

AIR, EXCESS WATER

BIOMASS HYDROTHERMAL DECOMPOSITION APPARATUS, METHOD THEREOF, AND ORGANIC MATERIAL PRODUCTION SYSTEM USING BIOMASS MATERIAL

TECHNICAL FIELD

The present invention relates to a biomass hydrothermal decomposition apparatus and a method thereof that enable efficient hydrothermal decomposition of biomass material, and to an organic material production system using biomass material, which system enables efficient production of organic materials such as alcohols, substitutes for petroleum, or amino acids by using such apparatus and method.

BACKGROUND ART

Technologies for producing ethanol or the like have been commercialized that involve converting woody biomass or other biomass into sugars with dilute sulfuric acid or concentrated sulfuric acid, and then subjecting them to solid-liquid separation, neutralizing the liquid phase thereof, and utilizing the resultant components as biomass materials for ethanol fermentation or the like (Patent Documents 1 and 2). Further, by using sugar as starting material, production of chemical industrial raw material (e.g., lactic fermentation) has been considered. Biomass as used herein refers to a living organism integrated in material circulation in the global biosphere or accumulation of organic materials derived from living organisms (see JIS K 3600 1258).

Sugarcane, corn, and other materials, currently used as alcohol raw materials, have been originally used for food. Using such food resources as long-term stable industrial resources is not preferable in view of life cycle of valuable food.

For this reason, it is a challenge to efficiently use cellulose resources such as herbaceous biomass and woody biomass, which are considered as potentially useful resources.

Cellulose resources include cellulose ranging from 38% to 50%, hemicelluloses components ranging from 23% to 32%, and lignin components, which are not used as fermentation materials, ranging from 15% to 22%. Due to many challenges, the industrial studies have been conducted targeting certain fixed materials, and no technologies have been disclosed yet on production systems taking into account diversity of the materials.

Production systems targeting fixed materials see almost no point regarding countermeasures for waste problems and global warming, because those systems have attempted such countermeasures with a method that brings more disadvantages to fermentation materials than starch materials. Thus, there has been a need for a method applicable to a variety of wastes in broader sense. Enzymatic saccharification methods are also considered as a future challenge due to its low efficiency. Acid treatment only achieves a low saccharification rate of about 75% (a basis for components that can be saccharified), due to excessive decomposition of sugar. Thus, the ethanol yield achieves only 25% by weight of cellulose resources (Non-Patent Document 1 and Patent Document 3).

[Patent Document 1] Japanese Patent Application Laid-open No. 9-507386

[Patent Document 2] Japanese Patent Application Laid-open No. 11-506934

[Patent Document 3] Japanese Patent Application Laid-open No. 2005-168335

[Non-Patent Document 1] Nikkei Biotechnology & Business, p. 52, September 2002

[Non-Patent Document 2] Biomass-Extensive Use of Bioresources, edited by Japanese Society for Bioscience, Biotechnology, and Agrochemistry, Asakura Publishing Co., Ltd., September 1985

DISCLOSURE OF INVENTION

Problem to be Solved by the Invention

In the proposals disclosed in Patent Documents 1 and 2 above, sulfuric acid necessary for reaction needs to be constantly supplied from outside the reaction system. With increasing the production scale, this poses problems, such as increasing the cost for purchasing equipment resistant to the acid and large amounts of sulfuric acid, while increasing the cost for disposing used sulfuric acid (e.g., cost for processing with a gypsum desulfulation), and the cost for recovering such sulfuric acid.

The proposal disclosed in Patent Document 3 above involves subjecting various types of cellulose resources to hydrothermal treatment, and converting them into sugars with enzymatic saccharification. During the hydrothermal treatment, cellulase inhibitors such as lignin components (Non-Patent Document 2) that inhibit enzymatic saccharification of cellulose are not removed and mixed with cellulose. This poses a problem of reducing the efficiency in cellulose enzymatic saccharification.

Other than cellulose, hemicellulose components are also contained in cellulose resources. This poses a problem that enzymes suitable for cellulose and hemicellulose components are necessary for enzymatic saccharification.

The resulting sugar solution includes a hexose solution from cellulose, and a pentose solution from hemicellulose components. For example, for alcohol fermentation, yeasts suitable for the respective solutions are necessary. Thus, alcohol fermentation needs to be improved low efficiency for fermenting a mixture of a hexose solution and a pentose solution.

As such, conventional technologies have caused a phenomenon that side reaction products inhibit enzymatic saccharification, reducing the sugar yield. Thus, what has been needed is a hydrothermal decomposition apparatus that removes inhibitors for enzymatic saccharification and thereby improves enzymatic saccharification of cellulose-based components.

In view of the foregoing problems, the present invention has an object to provide: a biomass hydrothermal decomposition apparatus and a method thereof that enable separation of cellulose-based components from biomass material; and an organic material production system using biomass material, which can efficiently produce a sugar solution using such apparatus and method, and can efficiently produce various types of organic materials (e.g., alcohols, substitutes for petroleum, or amino acids) using the sugar solution as a base material.

Means for Solving Problem

According to an aspect of the present invention, a biomass hydrothermal decomposition apparatus includes a biomass feeder that feeds biomass material under normal pressure to under increased pressure, a hydrothermal decomposition device that allows the fed biomass material to be gradually moved inside a device main body from either end thereof in a consolidated condition, and also allows hot compressed water to be fed from an other end of a feed section for the biomass material into the main body, so as to cause the biomass material and the hot compressed water to countercurrently contact with each other and undergo hydrothermal decomposition, and that elutes a lignin component and a hemicellulose component into the hot compressed water, so as to separate the lignin component and the hemicellulose component from the biomass material; and a biomass discharger that discharges, from the side where the hot compressed water is fed into the device main body, a biomass solid residue under increased pressure to under normal pressure.

Advantageously, the biomass hydrothermal decomposition apparatus further include a fixed stirring unit or a rotating stirring unit that stirs the biomass material inside the device main body.

Advantageously, in the biomass hydrothermal decomposition apparatus, the biomass feeder is a pressing unit that presses the biomass.

Advantageously, the biomass hydrothermal decomposition apparatus further includes an excess water drain line through which excess water is drained from pulverized biomass to be fed into the device main body.

Advantageously, the biomass hydrothermal decomposition apparatus further includes
a plurality of feed sections through which the hot compressed water is fed into the device main body, and a plurality of discharge sections through which discharged hot water is discharged from the device main body.

Advantageously, the biomass hydrothermal decomposition apparatus further includes a filter section that filtrates the discharged hot water to be discharged from the device main body.

Advantageously, the biomass hydrothermal decomposition apparatus further includes a density monitoring unit that monitors a biomass solid residue content inside the device main body.

Advantageously, in the biomass hydrothermal decomposition apparatus, the rotating stirring unit includes a scraper that prevents occlusion of an outlet for discharged hot water.

Advantageously, in the biomass hydrothermal decomposition apparatus, the hydrothermal decomposition device has a reaction temperature ranging from 180° C. to 240and has a condition of hot compressed water.

Advantageously, in the biomass hydrothermal fed biomass material and the fed hot compressed water is within 1:1 to 1:10.

According to another aspect of the present invention, a method for biomass hydrothermal decomposition includes feeding biomass material under normal pressure to under increased pressure, allowing the fed biomass material to be gradually moved inside a device main body from either end thereof in a consolidated condition and allowing hot compressed water to be fed from an other end of a feed section for the biomass material into the main body, so as to cause the biomass material and the hot compressed water to countercurrently contact with each other and undergo hydrothermal decomposition, eluting a lignin component and a hemicellulose component into the hot compressed water, so as to separate the lignin component and the hemicellulose component from the biomass material, and discharging, from the side where the hot compressed water is fed into the device main body, a biomass solid residue under increased pressure to under normal pressure.

According to still another aspect of the present invention, an organic material production system using biomass material includes a pretreatment device that pretreats the biomass material, the hydrothermal decomposition apparatus according to any one of the first to tenth inventions, a first enzymatic hydrolysis device that treats, with an enzyme, cellulose in a biomass solid residue discharged from the hydrothermal decomposition device, so as to enzymatically hydrolyze the cellulose to a sugar solution containing hexose; and a fermenter that produces, using the sugar solution obtained by the first enzymatic hydrolysis device, any one of alcohols, substitutes for petroleum, or amino acids by fermentation.

Advantageously, the organic material production system using biomass material includes a second enzymatic hydrolysis device that treats, with an enzyme, a hemicellulose component in discharged hot water, so as to enzymatically hydrolyze the hemicellulose component to a sugar solution containing pentose, and a fermenter that produces, using the sugar solution obtained by the second enzymatic hydrolysis device, any one of alcohols, substitutes for petroleum, or amino acids by fermentation.

EFFECT OF THE INVENTION

According to the present invention, with use of a hydrothermal decomposition apparatus that causes biomass material and hot compressed water to countercurrently contact with each other in a consolidated condition, side reaction products (lignin components and hemicellulose components) resulting from the reaction for producing a target component, i.e., cellulose, (that is enzymatically saccharified to a hexose solution) are transferred into the hot compressed water. In this way, the cellulose-based biomass solid residue can be obtained. Accordingly, by efficiently saccharifying it to the hexose solution and using the sugar solution as a substrate material, various types of organic materials (e.g., alcohols, substitutes for petroleum, or amino acids) can be produced efficiently.

By causing biomass material and hot compressed water to countercurrently contact with each other, their components are sequentially discharged to the outside the reaction system in order of solubility in the hot water. Further, due to the temperature gradient from a portion where the biomass is fed to a portion where the hot water is fed, excessive decomposition of hemicellulose components is prevented. As a result, pentose components can be recovered efficiently.

Figure 1:
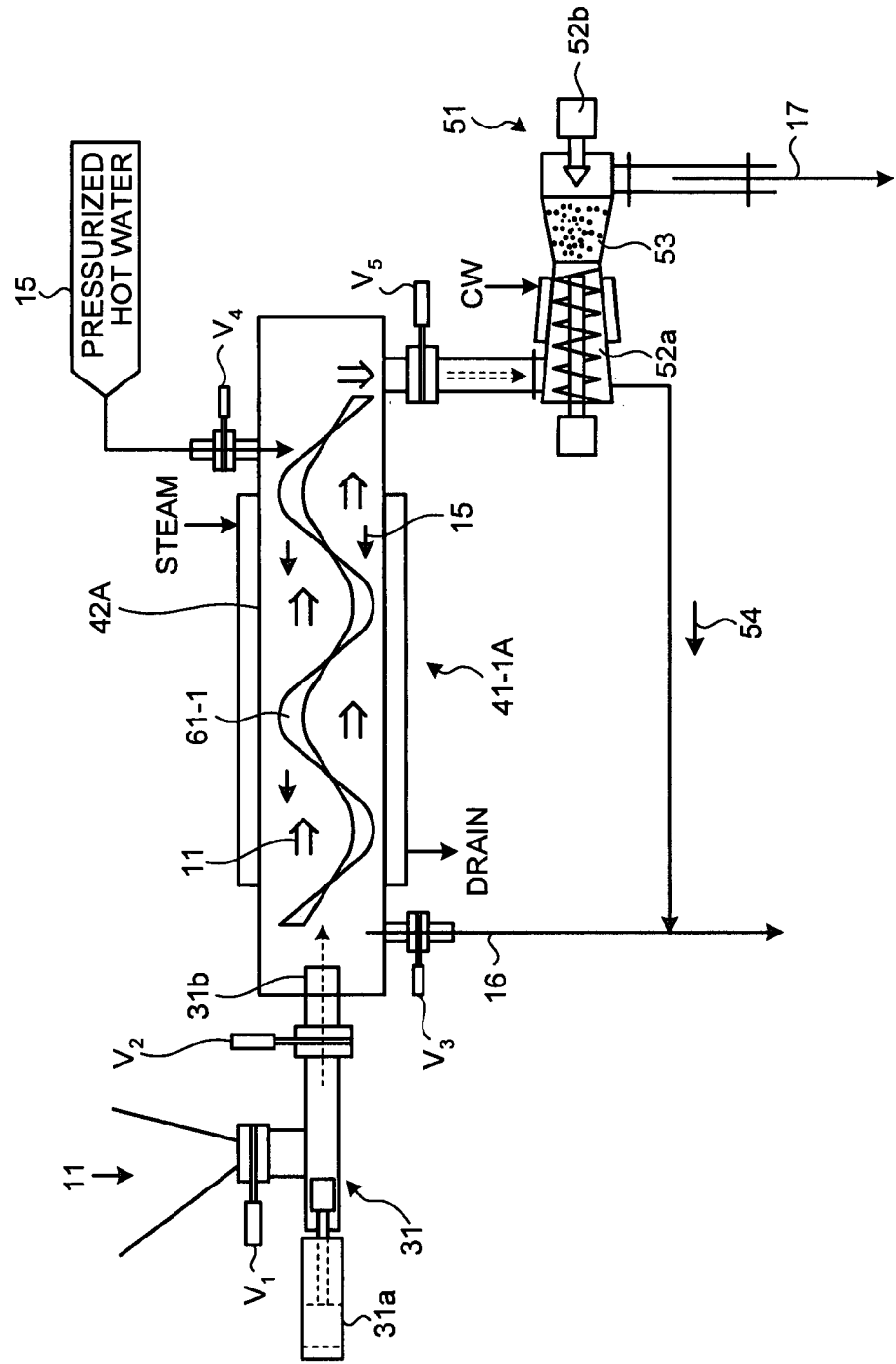
FIG. 1 is a schematic of a hydrothermal decomposition apparatus according to a first embodiment.

EXPLANATIONS OF LETTERS OR NUMERALS 10-1, 10-2 alcohol production system
11 biomass material
12 pretreatment device
13 pulverized biomass
41-1A to 41-1C,41-2, 41-3 hydrothermal decomposition device
15 hot compressed water
16 discharged hot water
17 biomass solid residue
18 enzyme
19 enzymatic hydrolysis device
19-1 first enzymatic hydrolysis device
19-2 second enzymatic hydrolysis device
20-1 first sugar solution (hexose)
20-2 second sugar solution (pentose)
23 ethanol

BEST MODE(S) FOR CARRYING OUT THE INVENTION

Exemplary embodiments of the present invention are described with reference to the accompanying drawings. The present invention is not limited to the embodiments. Constituting elements in the embodiments include elements easily achieved by a person skilled in the art, or elements being substantially equivalent to those elements.

First Embodiment

A biomass hydrothermal decomposition apparatus according to an embodiment of the present invention is described with reference to the drawings. FIG. 1 is a schematic of a biomass hydrothermal decomposition apparatus according to the embodiment. As shown in FIG. 1, a biomass hydrothermal decomposition apparatus 41-1A according to the present embodiment includes: a biomass feeder 31 that feeds biomass material (e.g., straw in the present embodiment) 11 under normal pressure to under increased pressure; a horizontal device main body (hereinafter, "device main body") 42A that allows the fed biomass material 11 to be gradually moved therethrough from an end on either the left or the right side (on the left side in the present embodiment) thereof in a consolidated condition, and also allows hot compressed water 15 to be fed therein from an end (on the right side in the present embodiment), which is different from the side from which the biomass material 11 is fed, so as to cause the biomass material 11 and the hot compressed water 15 to countercurrently contact with each other and undergo hydrothermal decomposition, and that transfers lignin components and hemicellulose components into the hot compressed water 15, so as to separate the lignin components and the hemicellulose components from the biomass material 11; and a biomass discharger 51 that discharges a biomass solid residue 17 under increased pressure to under normal pressure, at the side from which the hot compressed water 15 is fed into the device main body 42A. Examples of the biomass feeder 31 that feeds biomass under normal pressure to under increased pressure may include a pump unit such as a piston pump or a slurry pump.

In the present embodiment, inside the device main body 42A is provided a fixed stirring unit 61-1 that stirs the biomass material 11 in a consolidated condition, so called in plug flow. With this arrangement, the biomass material 11 fed therein is stirred by stirring action when moved axially.

By providing the fixed stirring unit 61-1, the pressurized water on the surface of the solid and inside the solid is progressively mixed in the device main body 42A, so that the reaction is facilitated.

According to the present invention, for the flowage of the hot compressed water 15 and the flowage of the biomass material 11 inside the device main body 42A of the hydrothermal decomposition apparatus 41-1A, the hot compressed water 15 and the biomass material 11 are countercurrently contacted, preferably with agitated flow.

The hydrothermal decomposition apparatus 41-1A performs decomposition in plug flow and has a simple configuration. Thus, the solid, the biomass material 11 is moved parallel to a central axis of its pipe, while being stirred in a direction perpendicular to the central axis of the pipe. On the contrary, the hot compressed water 15 (hot water, the liquid dissolving decomposed products) is moved while being soaked in solid particles by the counter-current flow against the solid.

In the plug flow, the hot compressed water 15 is flowed uniformly. This is because, when the solid biomass material 11 is decomposed in the hot compressed water 15, the decomposed products are dissolved in the hot water. Accordingly, the viscosity around a decomposed portion is increased, so that the hot water is moved toward an undecomposed portion dominantly, causing decomposition of the undecomposed portion. This creates a uniform flow of the hot water, enabling uniform decomposition.

In the device main body 42A of the hydrothermal decomposition apparatus 41-1A, due to the resistance of its inner pipe wall, the solid density at the outlet side for the biomass material 11 is reduced compared with that at the inlet side for the biomass material 11. In addition, the amount of the biomass solid residue 17 is reduced by the decomposition. As a result, the ratio of the hot compressed water 15 is increased, and the liquid retention time is prolonged, causing excessive decomposition of decomposed components in the liquid. For this reason, the fixed stirring unit can be provided as appropriate.

The fixed stirring unit 61-1 may have grooves formed thereon, or may be installed at various pitches. Further, the fixed stirring unit 61-1 may have screws in series at multiple stages, so that each screw performs stirring individually. The device main body 42A of the hydrothermal decomposition apparatus 41-1A may have a taper shape. Specifically, in the device main body 42A, the outlet for the biomass material 11 may have a smaller cross-sectional area than the inlet. With this arrangement, the solid density of the biomass material 11 is increased in the device main body 42A.

Further, an unstiffing function may be provided for preventing the solid from occluding the device main body 42A. Further, the solid-liquid weight ratio in the device main body 42A may be controlled appropriately by controlling, for example, the torque of a rotating stirring unit, the capacitance and the ultrasonic wave in the device main body 42A, and the weight of components inside the device main body 42A.

Biomass to be fed to the hydrothermal decomposition apparatus 41-1A is not limited to any specific type, and is a living organism integrated in material circulation in global biosphere or accumulation of organic materials derived from living organisms (see JIS K 3600 1258). In the present invention, particularly, cellulose resources of wood materials such as broadleaf trees and plant materials; agricultural wastes; and food wastes are preferably used.

The biomass material 11 is preferably broken into particles having a diameter of 5 millimeters or less, though not limited to this particle diameter. In the present embodiment, biomass may be subjected to pretreatment with pretreatment equipment such as pulverizing equipment, before being fed. In addition, biomass may be cleaned with cleaning equipment. When the biomass material 11 is rice husk, for example, the biomass material 11 can be fed to the hydrothermal decomposition apparatus 41-1A, without being subjected to pulverization.

In the hydrothermal decomposition apparatus 41-1A, the reaction temperature ranges from 180° C. to 240° C. preferably, and from 200° C. to 230° C. more preferably. This is because, at temperatures below 180° C., the hydrothermal decomposition takes place at a low rate and requires a longer time, increasing the apparatus size, which are not preferable. On the contrary, at temperatures above 240° C., the decomposition rate is too high and more cellulose components are transferred from the solid phase to the liquid phase, facilitating excessive decomposition of hemicellulose sugars, which are not preferable. Dissolution of hemicellulose components starts at about 140° C., dissolution of cellulose starts at about 230° C., and dissolution of lignin components starts at about 140° C. The temperature is preferably set within a range from 180° C. to 240° C. that allows cellulose to be remained in the biomass solid residue, and that enables hemicellulose components and lignin components to be decomposed at adequate rates.

The reaction pressure is preferably set to a pressure higher by 0.1 MPa to 0.5 MPa than the saturated vapor pressure of water at each temperature, which allows the hot compressed water to stay inside the device main body. The reaction time is preferably three minutes to ten minutes, not more than 20 minutes. This is because a longer reaction time increases the ratio of excessively decomposed products and is not preferable.

For these reasons, preferably, the hydrothermal decomposition apparatus 41-1A creates a uniform flow of hot compressed water while causing the biomass material 11 and the hot compressed water 15 to countercurrently contact with each other.

Figure 9:
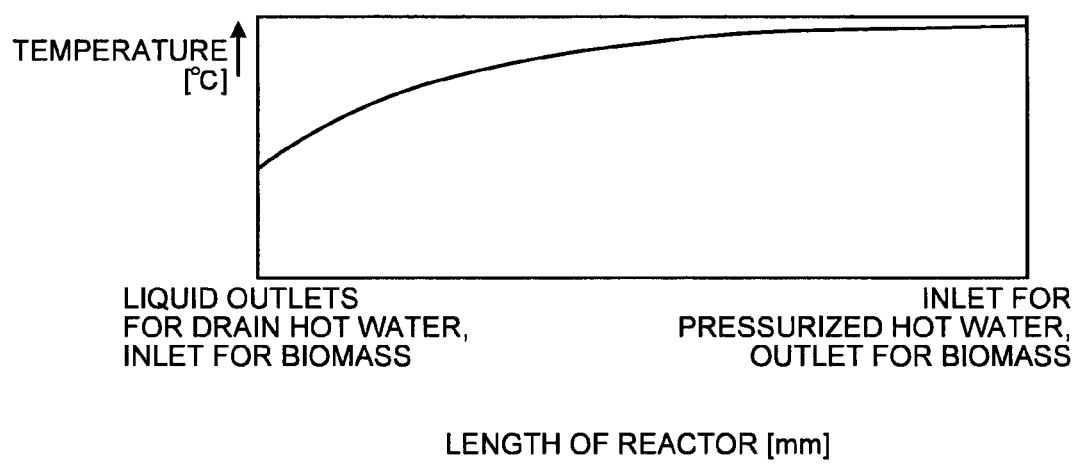
FIG. 9 is a graph of temperature distribution in a reactor.

The hot compressed water 15 is flowed by the counter-current flow, so that the heat is directly exchanged. This results in a temperature distribution as shown in FIG. 9, preventing excessive decomposition of decomposed products (such as lignin components), which are decomposed and discharged into the liquid.

The hot compressed water 15 to be fed into the device main body 42A is preferably less in weight relative to the biomass material 11, because it enables reduction in amount of steam used for warming during the hydrothermal decomposition. The weight ratio of the biomass material 11 and the hot compressed water 15 both to be fed is, for example, 1:1 to 1:10 preferably, and 1:1 to 1:5 more preferably, though it varies accordingly depending on the apparatus configuration. Particularly, in the present embodiment, the plug flow is composed of solid phase and liquid phase, i.e. the biomass material 11 and the hot compressed water 15, and is moved through the device main body 42A in the consolidated condition. The solid-to-liquid ratio can be 1:1 to 1:5. As described, the weight ratio of the biomass material 11 and the hot compressed water 15 both to be fed into the device main body 42A is made 1:1 to 1:10, thereby reducing the heat necessary for the hydrothermal decomposition apparatus.

Further, by controlling the solid-to-liquid weight ratio inside the device main body 42A, the conditions for hydrothermal decomposition are stabilized, and the biomass solid residue 17 is stably discharged from the biomass discharger 51.

By causing the biomass material 11 and the hot compressed water 15 to countercurrently contact with each other inside the hydrothermal decomposition apparatus 41-1A, the solid-liquid separation is performed. This reduces the amount of excessively decomposed products to be brought into the solid, cellulose. Because lignin components and the like are precipitated at low temperatures, the separation is difficult at low temperatures. Thus, after the hydrothermal decomposition, the decomposed products are taken out from the reaction system and subjected to the separation. In this way, it is possible to reduce the heat loss when flush occurs due to a transition from a high temperature and high pressure condition to a normal temperature and normal pressure condition. Further, the discharged liquid containing the decomposed products is separated with improved efficiency. This arrangement is realized considering the fact that the hydrothermal decomposition products are polysaccharide components precipitated at low temperatures and therefore the separation is hardly carried out at low temperatures.

According to the present embodiment, the weight of the biomass material 11 to be fed into the hydrothermal decomposition apparatus 41-1A is increased, relative to the weight of the hot compressed water 15. This enables reduction in the apparatus size, thus contributing to improve economic efficiency.

Inside the hydrothermal decomposition apparatus 41-1A, the temperature of the biomass material 11 is increased by causing it to contact the hot compressed water 15 in the device main body 42A and directly exchanging the heat. The temperature may be increased by using steam or the like from the outside as necessary. Alternatively, saturated steam may be directly fed into the device main body 42, instead of the hot water.

In the present embodiment, the biomass feeder 31 employs a mechanism for feeding the biomass material 11, including a piston pump 31a. With this arrangement, the biomass feeder 31 feeds the solid biomass material 11 under normal pressure to under increased pressure. By using the piston pump 31a and applying pressure with the piston, the biomass material 11 is reliably fed into the device main body 42A.

Specifically, use of the piston pump 31a enables the solid in the counter-current flow of solid and liquid, i.e., the biomass material 11, to be moved by operation of the piston pump 31a, without providing a rotational moving unit or the like for moving the solid inside the device main body 42A. Further, use of the piston pump 31a also enables control of the density inside the device main body 42A (the solid-to-liquid weight ratio). Specifically, it is possible to control the retention time of the hot compressed water inside the device main body 42A.

The biomass discharger 51 employs a feeding mechanism including a screw feeder 52a and a hydraulic cylinder 52b. This enables the solid reacted inside the hydrothermal decomposition apparatus 41-1A to be compressed, so that a biomass plug 53 is formed. The biomass plug 53 serves as a material seal for keeping the pressure inside the hydrothermal decomposition apparatus 41-1A. Gradually pressed by the screw feeder 52a, the biomass under the increased pressure can be gradually discharged from an edge of the hydraulic cylinder 52b to under the normal pressure. When the biomass solid residue 17 compressed, the residual water is removed from the biomass plug 53.

This dewatered solution 54 includes components soluble in hot compressed water (lignin components and hemicellulose components). Thus, the dewatered solution 54 is treated together with the discharged hot water 16.

As a result, it is possible to dewater the hot compressed water containing the components soluble in the hot compressed water and normally accompanying the biomass solid residue 17. This improves the yield of pentose using hemicellulose components (described later), while contributing to reduce accompanied hexose enzyme inhibitors (e.g., lignin components).

Because the pressure is changed from increased pressure to normal pressure inside the biomass discharger 51, the biomass solid residue 17 to be discharged is steam-exploded, causing breakage of its fiber structure. This improves the efficiency of enzymatic saccharification in the subsequent process.

The biomass discharger 51 can remove both of enzymatic saccharification inhibitors and ethanol fermentation inhibitors, or either of them, which are low-molecular-weight volatile inhibitors.

In the present embodiment, the hot compressed water is discharged at a portion near the inlet for feeding the biomass. Alternatively, a liquid outlet for the hot compressed water may be provided in a middle portion and the discharged liquid may be subjected to either or both of heating and cooling so that an ideal temperature distribution is plotted. Then, the discharged liquid may be fed into the device main body 42A again.

The concentration of inhibitors such as furfral in the liquid may be measured near a discharged section for the hot compressed water, so that the feed amount of the hot compressed water 15 is controlled based on the measured value. Alternatively, the sugar concentration may be measured near the biomass discharger 51, so that the feed amount of the hot compressed water 15 is controlled based on the measured value.

In the present embodiment, the hot compressed water 15 may be fed from one section. The present invention is not limited to this, and the hot compressed water 15 may be fed from a plurality of sections for temperature control.

In the present invention, by causing biomass material and hot compressed water to countercurrently contact with each other, their components are sequentially discharged in order of solubility in the hot water. Further, due to the concentration gradient and the temperature gradient from where the biomass is fed to where the hot water is fed, excessive decomposition of hemicellulose components is prevented. As a result, pentose components can be recovered efficiently. Further, by causing the biomass material and the hot compressed water to countercurrently contact with each other, the heat is recovered, which is preferable in view of system efficiency.

Figure 2:
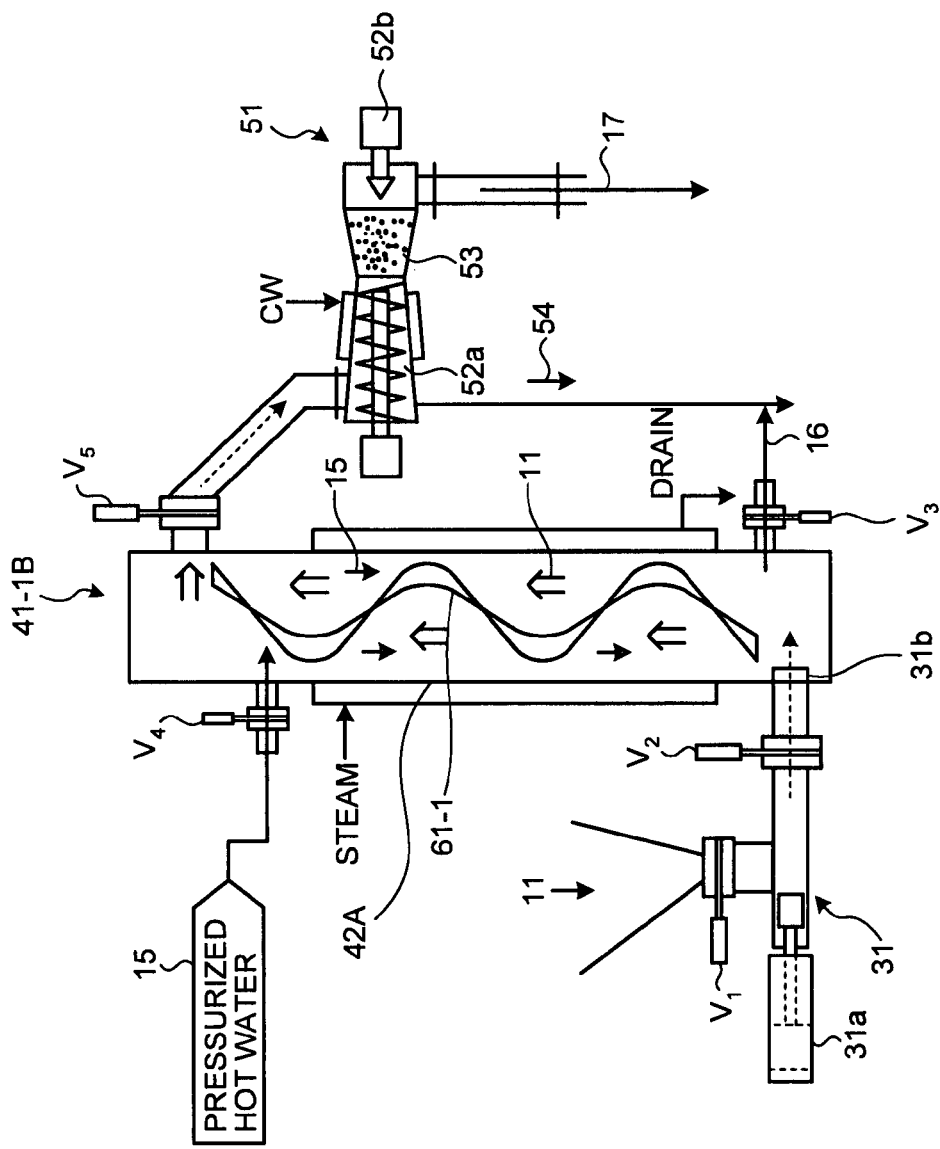
FIG. 2 is a schematic of another hydrothermal decomposition apparatus according to a first embodiment.

FIG. 2 depicts a modification of the present embodiment. As shown in FIG. 2, a hydrothermal decomposition apparatus 41-1B is a vertical type of the horizontal type shown in FIG. 1. As shown in FIG. 2, the biomass feeder 31 is provided near a lower end of the device main body 42A, so that the biomass material 11 is fed from the lower end, while the hot compressed water 15 is fed from an upper end thereof. By causing the biomass material 11 and the hot compressed water 15 to countercurrently contact with each other, their components are sequentially discharged as the discharged hot water 16, in order of solubility in the hot compressed water 15. Further, the biomass solid residue 17 is discharged from the biomass discharger 51 provided near the upper end.

In the present embodiment, the device main body is arranged as a vertical type. The present invention is not limited to this, and the device main body may be a slanted type. The device main body may be arranged as a slanted type or a vertical type, because it is preferable regarding that the gas resulting from the hydrothermal decomposition reaction, the gas brought into the biomass material, and the like can be released quickly from the upper side. This arrangement is also preferable in view of the discharging efficiency, because decomposed products are discharged with the hot compressed water 15 and therefore the concentration of the discharged materials is increased from the upper side to the lower side.

Figure 3:
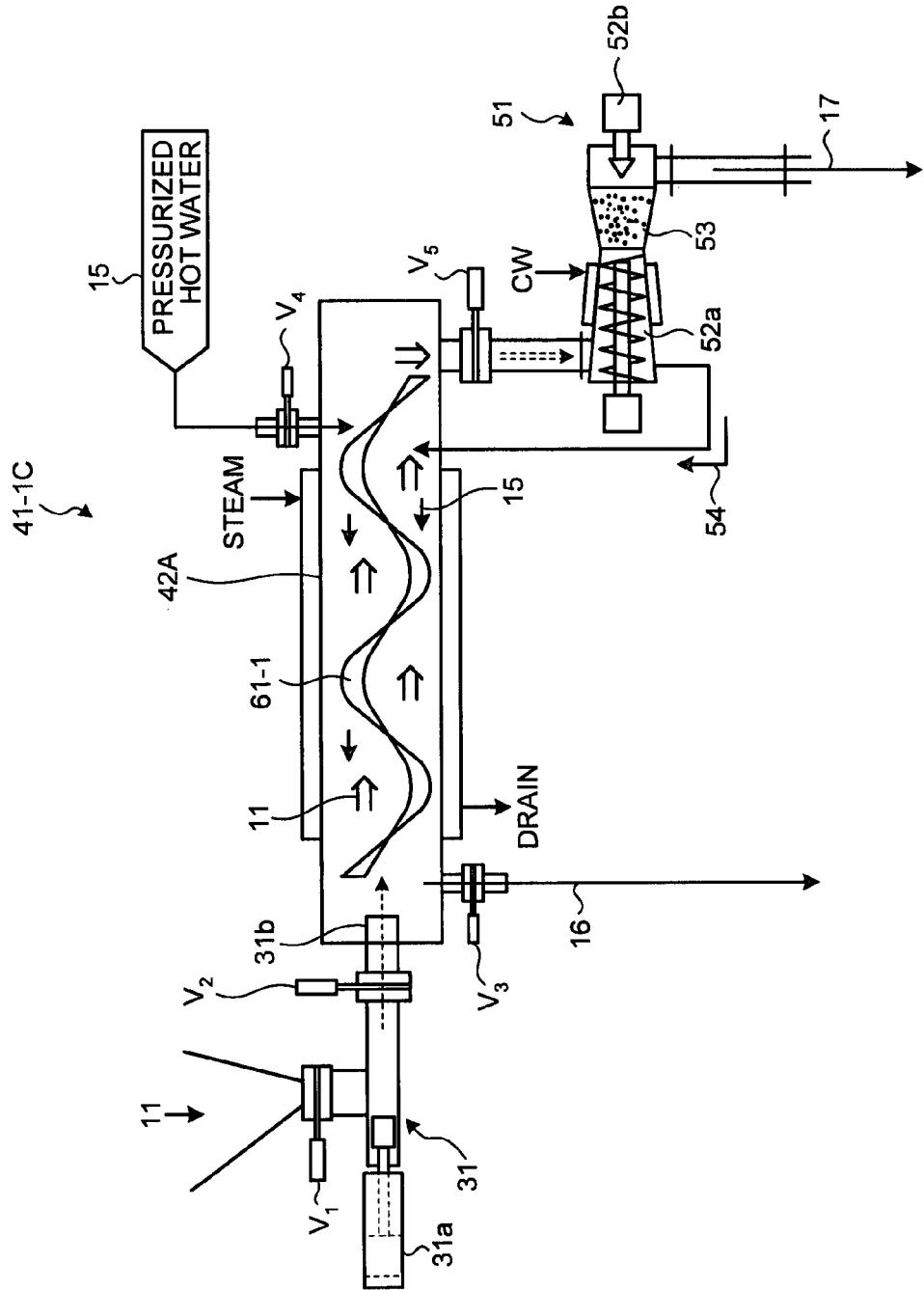
FIG. 3 is a schematic of another hydrothermal decomposition apparatus according to a first embodiment.

FIG. 3 depicts a modification of the present embodiment. In a hydrothermal decomposition apparatus 41-1C shown in FIG. 3, the dewatered solution 54, separated in the biomass discharger 51, is fed again into the device main body 42A. This arrangement reduces the amount of the hot compressed water to be fed into the apparatus. Further, a desirable counter-current flow is realized.

Figure 4:
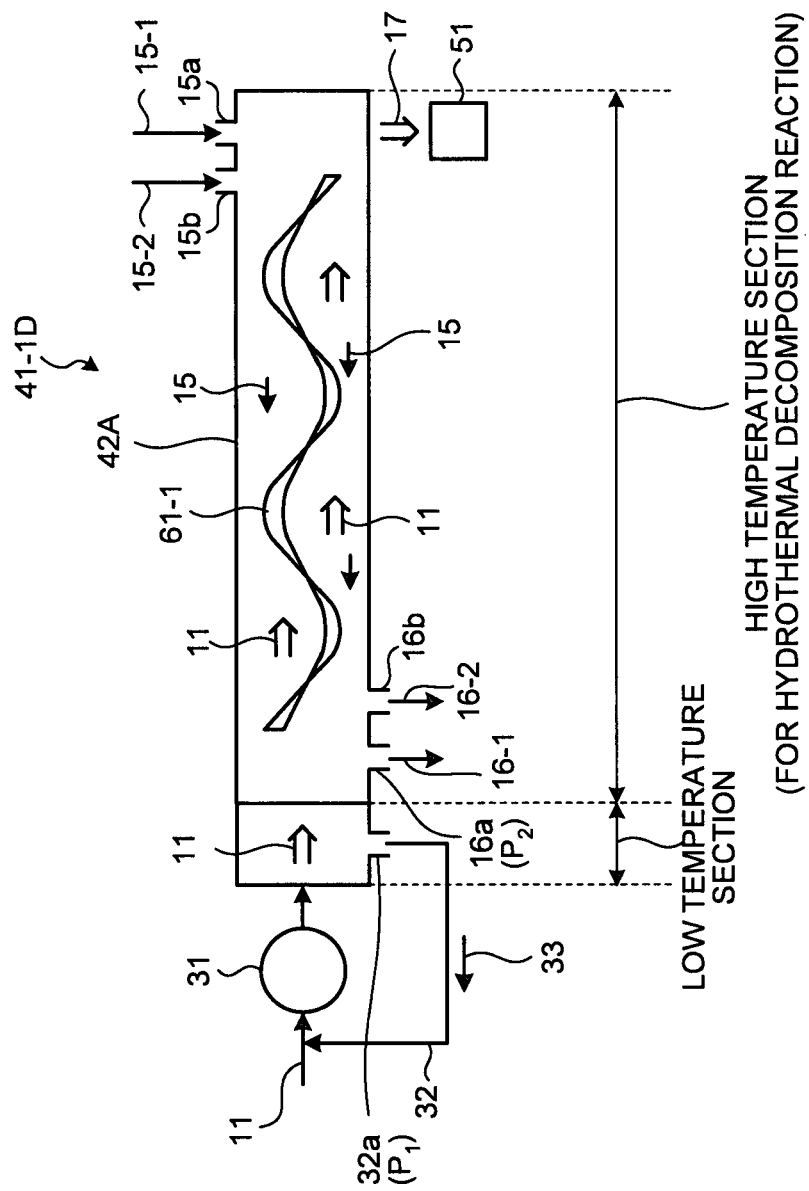
FIG. 4 is a schematic of another hydrothermal decomposition apparatus according to a first embodiment.

FIG. 4 depicts another modification of the present embodiment. As shown in FIG. 4, a hydrothermal decomposition apparatus 41-1D includes an excess water removal line 32, so that excess water 33 contained in the biomass is removed from the section for feeding the biomass material 11 into the device main body 42A. The excess water may be used to make the biomass material 11 wet. Specifically, an excess water outlet 32a is provided away from a liquid outlet 16a for the discharged hot water 16-1, and the pressure ($P_1$) at the excess water outlet 32a is made greater than the pressure ($P_2$) at the liquid outlet 16a. In this way, the amount of the liquid to be discharged is controlled. This arrangement prevents the reverse flow and excessive decomposition, while reducing the heat loss.

The liquid outlet for the discharged hot water may be provided at a plurality of sections (two sections 16a and 16b in the present embodiment), and the properties of the discharged hot water at the liquid outlet(s) and/or the properties of the biomass solid residue may be measured. Then, based on the measured values, the liquid outlet(s) for the discharged hot water may be changed appropriately. In this way, the decomposition time is controlled.

Further, a hot water inlet for the hot compressed water may be provided at a plurality of sections (two sections 15a and 15b in the present embodiment), and either or both of the properties of the discharged hot water at the liquid outlet(s) and the properties of the solid at the outlet may be measured. Then, based on the measured values, the liquid outlet(s) for the discharged hot water may be changed. In this way, the decomposition time is controlled.

The feed amount of the biomass material 11 and the amount of the discharged hot water at the liquid outlet(s) may be controlled so that the solid-to-liquid weight ratio becomes a predetermined value in the hydrothermal decomposition apparatus 41-1D.

Figure 5:
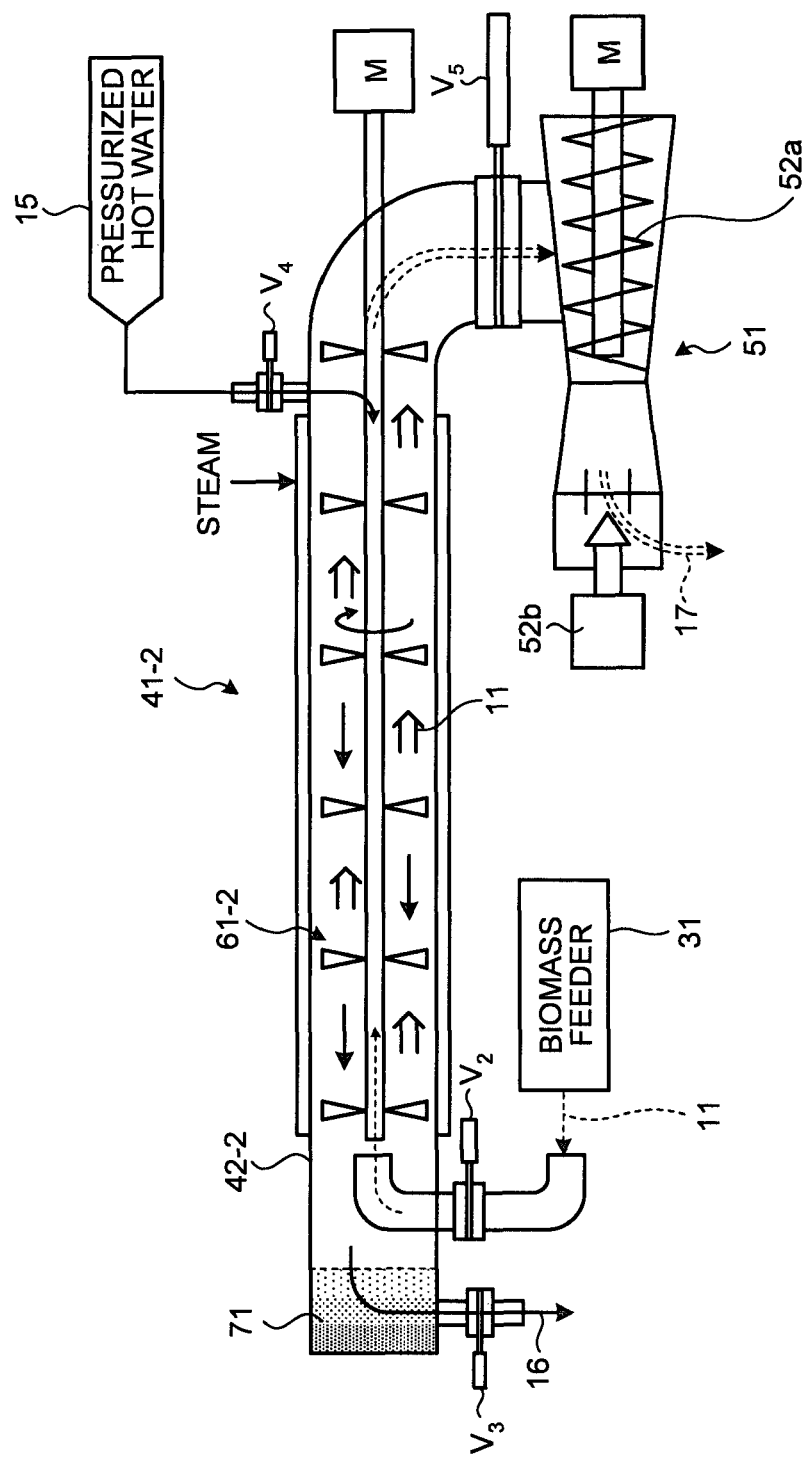
FIG. 5 is a schematic of another hydrothermal decomposition apparatus according to a first embodiment.

FIG. 5 depicts still another modification of the present embodiment. As shown in FIG. 5, a rotating stirring unit 61-2 may be provided inside a device main body 42-2 so that the biomass material 11 and the hot compressed water 15 may actively and countercurrently contact with each other to be mixed and stirred.

The rotating stirring unit 61-2 may have grooves formed thereon, or may be installed at various pitches. Further, the rotating stirring unit 61-2 may have screws in series at multiple stages, so that each screw performs stirring individually.

Further, a filter unit 71 is provided through which the hot water 16 is discharged from the device main body 42-2, as shown in FIG. 5.

With straw biomass for example, its consolidated layer with a thickness of a several centimeters can serve as a material seal. The consolidated layer having a thickness equal to or less than that thickness allows the liquid to pass therethrough, thus serving as a self filter and enabling the liquid-solid separation at the liquid outlet(s). Alternatively, a scraper mechanism (not shown) for maintaining a predetermined thickness may be provided. In addition to the self filter, a sand filtration filter may be provided.

The scraper mechanism may be controlled by the pressure at the liquid outlet(s).

Figure 6:
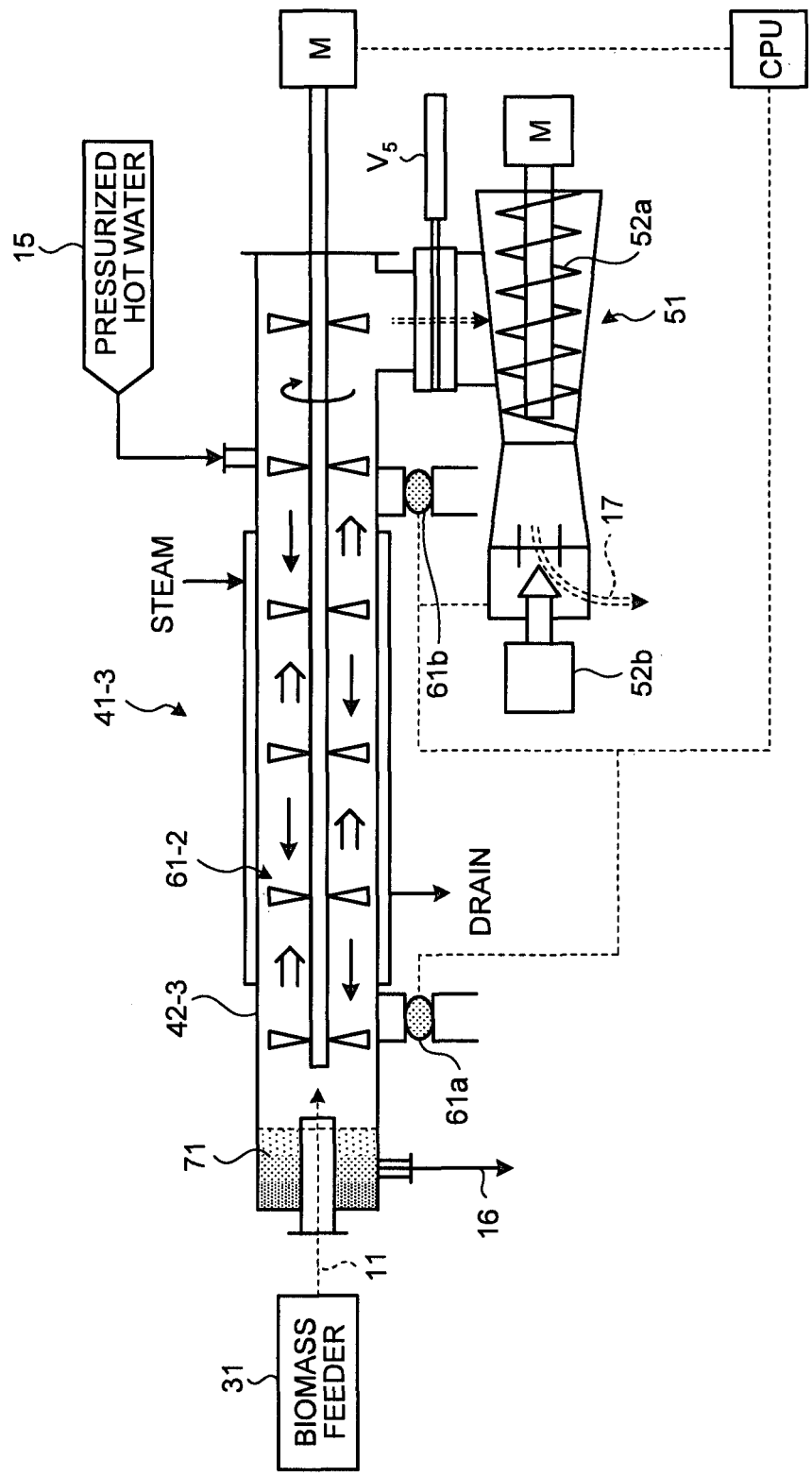
FIG. 6 is a schematic of another hydrothermal decomposition apparatus according to a first embodiment.

FIG. 6 depicts still another modification of the present embodiment. As shown in FIG. 6, a device main body 42-3 of a hydrothermal decomposition apparatus 41-3 includes load cells 61a and 61b as units each monitoring a concentration of the solid inside the device main body 42-3. The load cells 61a and 61b detect the weight of the solid, and change the rotation number and the rotation direction of the paddles, so as to control the concentration. In this way, the reaction efficiency is improved.

Figure 7:
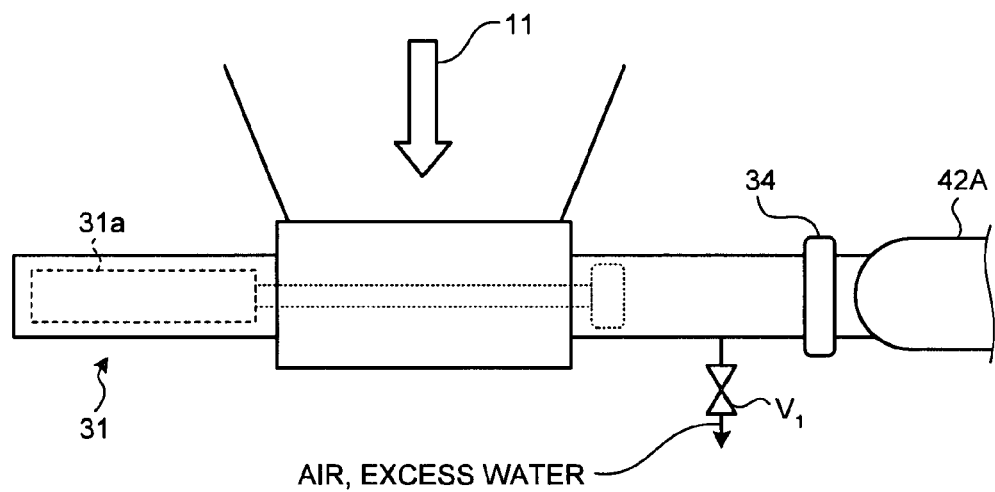
FIG. 7 is a schematic view of a biomass feeder according to the first embodiment.
Figure 8:
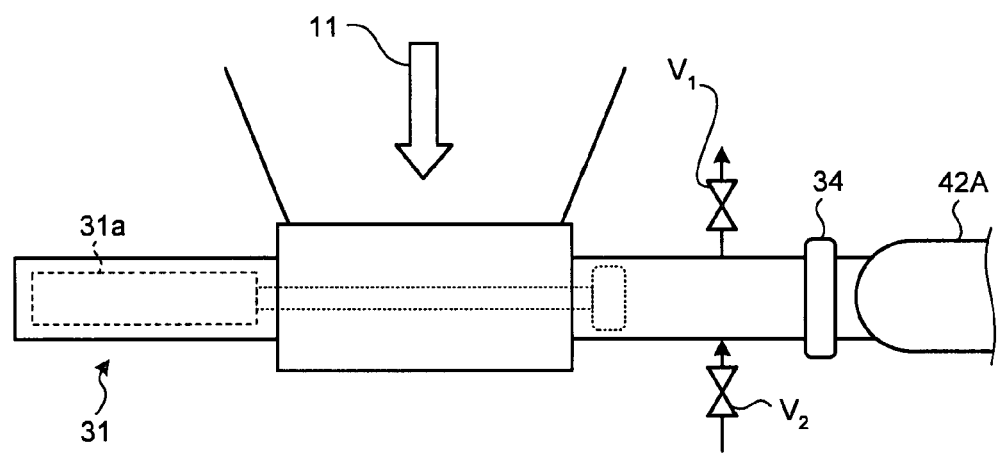
FIG. 8 is a schematic view of another biomass feeder according to the first embodiment.

Referring to FIGS. 7 and 8, the following describes an injection method using a piston pump as a pressing unit, for injecting the biomass material 11 into the device main body 42-3. As a pressing unit, for example, a slurry pump or a screw feeder may be used appropriately, other than the piston pump.

As shown in FIG. 7, the biomass material 11, which has been made wet, is consolidated in the cylinder. If a consolidation force is equal to or less than a set value, air and excess water are discharged from an opened air/excess water discharge valve $V_1$. When the consolidation force reaches the set value, the air/excess water discharge valve $V_1$ is closed. With this arrangement, the biomass material 11 may be filled via a gate valve 34 into the device main body 42A of the hydrothermal decomposition apparatus.

When the biomass material is a dried material (containing little water), the material is consolidated in the cylinder. If a consolidation force is equal to or less than a set value, air is discharged from the opened air/excess water discharge valve $V_1$. When the consolidation force reaches the set value, water is fed from a water feeding valve $V_2$, excess water is discharged from the air/excess water discharge valve $V_1$, and the both valves are closed. With this arrangement, the biomass material 11 may be filled via the gate valve 34 into the device main body 42A of the hydrothermal decomposition apparatus.

In the first embodiment, constituting elements of the biomass hydrothermal decomposition apparatus are described individually with reference to FIGS. 1 to 8. These elements may be combined appropriately.

Second Embodiment

Figure 10:
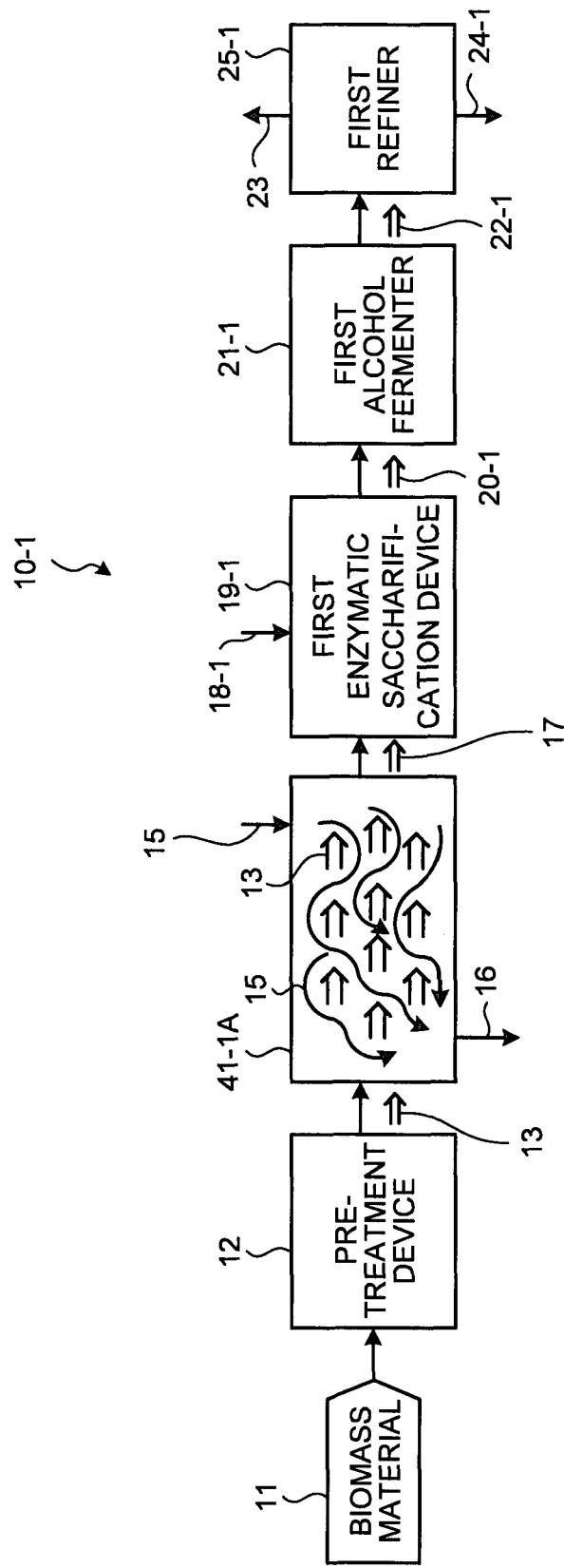
FIG. 10 is a schematic of an alcohol production system according to a second embodiment.

With reference to the drawings, the following describes a system of producing an organic material, i.e., alcohol, with use of biomass material according to an embodiment of the present invention. FIG. 10 is a schematic of an organic material production system using biomass material according to the embodiment. As shown in FIG. 10, an alcohol production system 10-1 using biomass material according to the present embodiment includes: a pretreatment device 12 that pulverizes the biomass material 11; the hydrothermal decomposition apparatus 41-1A (shown in FIG. 1) that hydrothermally decomposes pulverized biomass 13 by causing it to countercurrently contact the hot compressed water 15, transfers lignin components and hemicellulose components into the hot compressed water 15, and separates the lignin components and the hemicellulose components from the biomass; a first enzymatic hydrolysis device 19-1 that treats cellulose in the biomass solid residue 17, discharged from the hydrothermal decomposition apparatus 41-1A, with an enzyme (cellulase) 18-1 to enzymatically hydrolyze it to a sugar solution containing hexose; a first alcohol fermenter 21-1 that produces an alcohol (ethanol in the present embodiment) by fermentation using a first sugar solution (hexose) 20-1 obtained by the first enzymatic hydrolysis device 19-1; and a first refiner 25-1 that refines a first alcohol fermentation liquid 22-1, so as to separate it into a target product, i.e., ethanol 23, and a residue 24-1.

According to the present invention, in the hydrothermal decomposition apparatus 41-1A shown in FIG. 1, use of the counter-current flow transfers lignin components and hemicellulose components to the liquid phase, i.e., the hot compressed water 15, while allowing cellulose to remain in the solid, i.e., the biomass solid residue 17. In this way, the first sugar solution (hexose) 20-1 is obtained at the first enzymatic hydrolysis device 19-1 for performing enzymatic saccharification. Accordingly, it is possible to establish a fermentation process suitable for a hexose (fermentation suitable for an end product: in the present embodiment, fermentation for obtaining the ethanol 23 using the first alcohol fermenter 21-1).

Although the present embodiment describes an example that an alcohol, ethanol, is obtained by fermentation, the present invention is not limited to this example. Other than alcohols, substitutes for petroleum used as chemical product material, or amino acids used as food and feed materials can be obtained with a fermenter.

Examples of industrial products produced from a sugar solution as a base material may include liquefied petroleum gas (LPG), auto fuel, aircraft jet fuel, heating oil, diesel oil, various types of heavy oils, fuel gas, naphtha, and naphtha decomposed products such as ethylene glycol, ethanolamine, alcohol ethoxylate, vinyl chloride polymer, alkylaluminum, polyvinyl acetate (PVA), vinyl acetate emulsion, polystyrene, polyethylene, polypropylene, polycarbonate, methyl methacrylate (MMA) resin, nylon, and polyester. Thus, substitutes for industrial products derived from crude oil, which is fossil fuel, and sugar solution derived from biomass, which is a biomass material for producing such substitutes, can be used efficiently.

Third Embodiment

Figure 11:
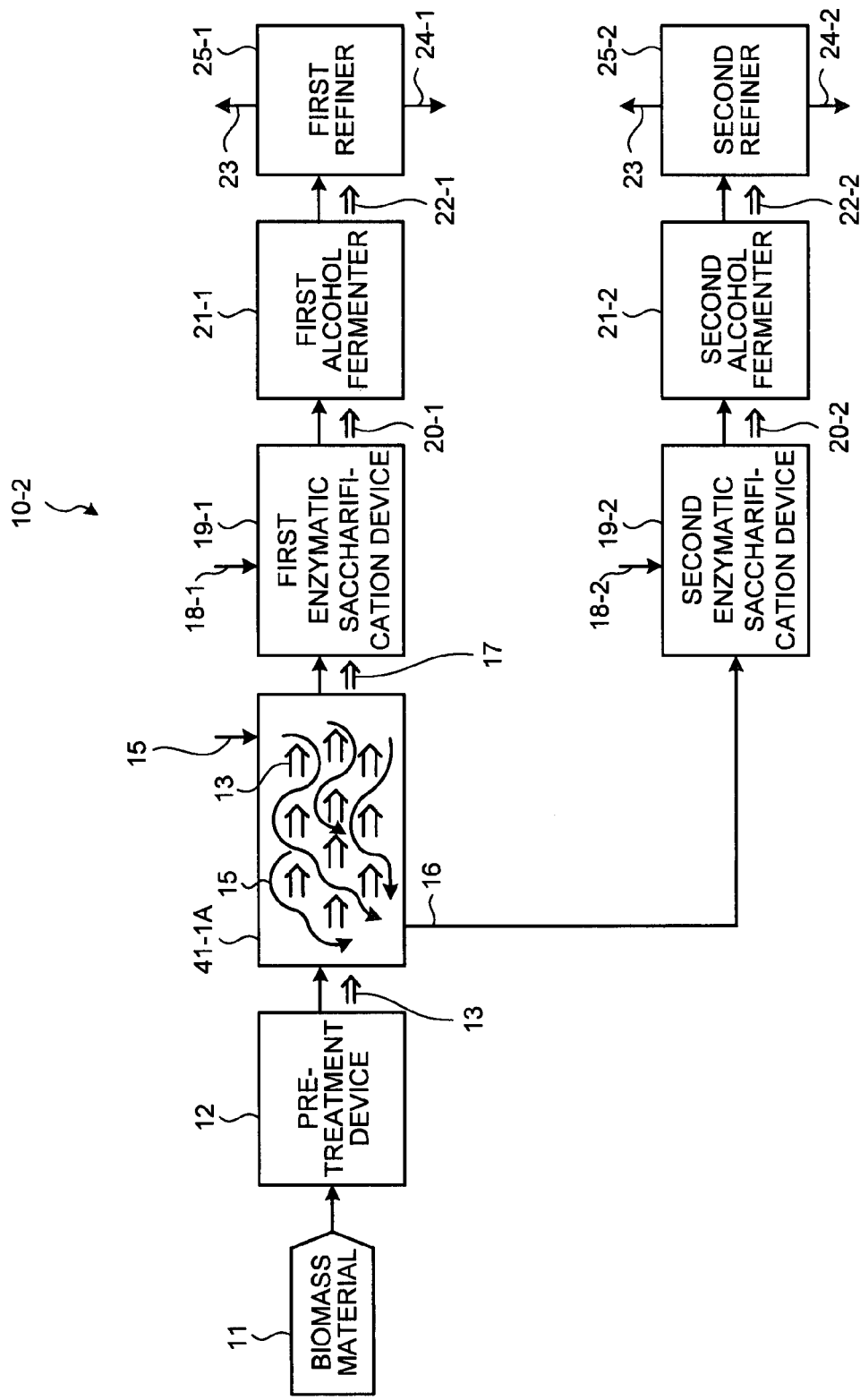
FIG. 11 is a schematic of an alcohol production system according to a third embodiment.

With reference to the drawings, the following describes a system of producing an organic material, i.e., alcohol, with use of biomass material according to an embodiment of the present invention. FIG. 11 is a schematic of a system of producing an organic material, i.e., alcohol, with use of biomass material according to the present embodiment. As shown in FIG. 11, an alcohol production system 10-2 using biomass material according to the present embodiment is constituted by the alcohol production system 10-1 shown in FIG. 10 that includes a second enzymatic hydrolysis device 19-2. The second enzymatic hydrolysis device 19-2 treats hemicellulose components, transferred into the hot water 16 discharged from the hydrothermal decomposition apparatus 41-1A, with an enzyme to enzymatically hydrolyze it to a sugar solution 20-2 containing pentose. Two enzymatic hydrolysis devices, two alcohol fermenters, and two refiners are provided (the first enzymatic hydrolysis device 19-1, the second enzymatic hydrolysis device 19-2, the first alcohol fermenter 21-1, a second alcohol fermenter 21-2, the first refiner 25-1, and a second refiner 25-2). The ethanol 23 is obtained by performing an enzymatic hydrolysis process, an alcohol fermentation process, and an alcohol refining process that are suitable for each of the first sugar solution (hexose) 20-1 and a second sugar solution (pentose) 20-2.

In the present embodiment, the ethanol 23 can be produced by fermentation, using the second sugar solution (pentose) 20-2 obtained by the second enzymatic hydrolysis device 19-2.

The discharged hot water is not necessarily treated in a separate system. For example, processes subsequent to the enzymatic hydrolysis devices, processes subsequent to the alcohol fermenters, or processes subsequent to the refiners may be arranged as common processes, or other modification may be made appropriately.

According to the present invention, in the hydrothermal decomposition apparatus 41-1A, use of the counter-current flow allows cellulose to remain in the solid phase which is the biomass solid residue 17. Accordingly, the first sugar solution (hexose) 20-1 is obtained by the first enzymatic hydrolysis device 19-1 for performing enzymatic saccharification. Further, hemicellulose components dissolved in the liquid phase which is the hot compressed water 15, are separated therefrom as the discharged hot water 16, so that the second sugar solution (pentose) 20-2 is obtained by the second enzymatic hydrolysis device 19-2 for separately performing enzymatic saccharification. This enables the solid and the liquid to be separated efficiently and saccharified individually. Accordingly, fermentation processes suitable for hexose and pentose (fermentation suitable for an end product: e.g., ethanol fermentation) can be established.

As such, in the hydrothermal decomposition apparatus 41-1A, use of the counter-current flow transfers a side reaction product and a lignin component soluble in hot compressed water, both acting as inhibitors during enzymatic saccharification reaction for obtaining hexose, to the hot compressed water 15. Accordingly, the cellulose-based biomass solid residue 17 is obtained, improving the yield of hexose in the subsequent enzymatic saccharification reaction.

On the other hand, hemicellulose components contained in the separated discharged hot water 16 is saccharified later at the second enzymatic hydrolysis device 19-2, so that a sugar solution containing pentose can be obtained. Then, by using yeasts etc. suitable for hexose and pentose, ethanol can be obtained by fermentation individually and efficiently.

As described above, the present invention provides: a biomass hydrothermal decomposition apparatus and a method thereof that can produce, by transferring cellulose-based components and hemicellulose components from the biomass material to the hot compressed water and separating them from each other, sugar solutions suitable for the cellulose-based components and the hemicellulose components (hexose sugar solution and pentose sugar solution), and that can efficiently produce, using the sugar solutions as substrate materials, various types of organic materials (e.g., alcohols, substitutes for petroleum, or amino acids); and an organic material production system using biomass material. However, a conventional technology causes a phenomenon that a side reaction product inhibits enzymatic saccharification and a sugar yield is reduced.

Industrial Applicability

As described, according to the present invention, a hydrothermal decomposition apparatus separates cellulose-based components from biomass material, so as to efficiently produce a sugar solution. Further, using the sugar solution as a substrate material, various types of organic materials (e.g., alcohols, substitutes for petroleum, or amino acids) can be efficiently produced.

The invention claimed is:

1. A biomass hydrothermal decomposition apparatus comprising:
    a biomass feeder having a piston pump for pressing biomass material so as to make the biomass material consolidated and feeding the consolidated biomass material via a valve;
    a hydrothermal decomposition device including:
    a device main body for countercurrently contacting the consolidated biomass material with a decomposition liquid essentially consisting of hot compressed water and hydrothermally decomposing the consolidated biomass, so as to elute a lignin component and a hemicellulose component into the hot compressed water and separate the lignin component and the hemicellulose component from the consolidated biomass material,
    a biomass material inlet provided on one side of the device main body, for supplying the consolidated biomass material into the device main body,
    a hot compressed water inlet provided on other side of the device main body, for supplying the decomposition liquid into the device main body,
    a discharged hot water outlet provided on the one side of the device main body, for discharging the hot compressed water with the lignin component and the hemicellulose component as a discharged hot water from the device main body, and
    a biomass solid residue outlet provided on the other side of the device main body, for discharging a biomass solid residue from the device main body,
    a biomass discharger that discharges the biomass solid residue from the biomass solid residue outlet under increased pressure to a decreased pressure, wherein
    the hydrothermal decomposition device further includes an excess water removal line for supplying a part of the discharged hot water as an excess water from the downstream of the discharged hot water outlet with respect to a flow direction from the hot compressed water inlet to the discharged hot water outlet to upstream of the biomass feeder,
    the hydrothermal decomposition device has a reaction temperature ranging from 180° C. to 240° C. and has a condition of hot compressed water;
    wherein a weight ratio of the fed consolidated biomass material and the fed hot compressed water is within 1:1 to 1:10;
    wherein a pressure higher by 0.1 MPa to 0.5 MPa is added to saturated vapor pressure of water at each temperature of the reaction temperature;
    wherein a reaction time is not more than 20 minutes; and
    wherein the consolidated biomass material are moved from the biomass material inlet to the biomass solid residue outlet by the piston pump.

2. The biomass hydrothermal decomposition apparatus according to claim 1, further comprising a fixed stirring unit or a rotating stirring unit that stirs the consolidated biomass material inside the device main body, wherein the rotating stirring unit has a rotation axis and a plurality of rotatable paddles that are provided at predetermined intervals of the rotation axis.

3. The biomass hydrothermal decomposition apparatus according to claim 1, further comprising:
    another hot compressed water inlet for supplying the decomposition liquid into the device main body; and
    a discharged hot water outlet for discharging the hot compressed water from the device main body.

4. The biomass hydrothermal decomposition apparatus according to claim 1, further comprising a filter section that filtrates the discharged hot water to be discharged from the device main body, the filter section being provided upstream of the discharged hot water outlet and in the device main body.

5. The biomass hydrothermal decomposition apparatus according to claim 1, further comprising a density monitoring unit that detects a weight of a biomass solid residue content inside the device main body.

6. The biomass hydrothermal decomposition apparatus according to claim 2, wherein the rotating stirring unit includes a scraper that prevents occlusion of the discharged hot water outlet.

7. The biomass hydrothermal decomposition apparatus according to claim 1, wherein the hydrothermal decomposition apparatus is a gradient type or a vertical type.

8. The biomass hydrothermal decomposition apparatus according to claim 1, wherein the biomass solid residue is suitable as a raw material for saccharification.

9. The biomass hydrothermal decomposition apparatus according to claim 1, wherein the biomass feeder further comprises a water feeding apparatus for feeding water therein.

10. The biomass hydrothermal decomposition apparatus according to claim 1, wherein the device main body has a taper shape whose cross-sectional area decreases from the biomass material inlet to the biomass solid residue outlet.

11. The biomass hydrothermal decomposition apparatus according to claim 1, wherein the biomass discharger includes
a compressing mechanism for compressing the biomass solid residue so as to remove residual water from the biomass solid residue and
a residual water outlet for discharging the residual water.

12. A method for biomass hydrothermal decomposition comprising:
pressing biomass material so as to make the biomass material consolidated and feeding the consolidated biomass material;
supplying the consolidated biomass material into a device main body of a hydrothermal decomposition device;
supplying a decomposition liquid essentially consisting of hot compressed water into the device main body;
countercurrently contacting the consolidated biomass material with the decomposition liquid and hydrothermally decomposing the consolidated biomass, so as to elute a lignin component and a hemicellulose component into the hot compressed water and separate the lignin component and the hemicellulose component from the consolidated biomass material,
discharging the hot compressed water with the lignin component and the hemicellulose component as a discharged hot water from the device main body, and
discharging a biomass solid residue from the device main body,
discharging the biomass solid residue from an increased pressure to a decreased pressure, wherein
the method further comprising supplying a part of the discharged hot water as an excess water to the biomass material before making the biomass material consolidated,
a reaction temperature of the hydrothermal decomposition ranges from 180° C. to 240° C. and an interior of the device is in a condition of hot compressed water;
wherein a weight ratio of the fed consolidated biomass material and the fed hot compressed water is within 1:1 to 1:10;
wherein a pressure higher by 0.1 MPa to 0.5 MPa is added to saturated vapor pressure of water at each temperature of the reaction temperature;
wherein a reaction time is not more than 20 minutes and
wherein the pressing biomass material causes the consolidated biomass material in the device main body to move from the biomass material inlet to the biomass solid residue outlet.

13. The method according to claim 12, wherein the biomass solid residue is suitable as a raw material for saccharification.

14. An organic material production system using biomass material, the organic material production system comprising:
a pretreatment device that pretreats the biomass material;
the hydrothermal decomposition apparatus according to claim 1;
a first enzymatic hydrolysis device that treats, with an enzyme, cellulose in a biomass solid residue discharged from the hydrothermal decomposition device, so as to enzymatically hydrolyze the cellulose to a sugar solution containing hexose; and
a fermenter that produces, using the sugar solution obtained by the first enzymatic hydrolysis device, any one of alcohols, substitutes for petroleum, or amino acids by fermentation.

15. The organic material production system using biomass material according to claim 14, comprising:
a second enzymatic hydrolysis device that treats, with an enzyme, a hemicellulose component in discharged hot water, so as to enzymatically hydrolyze the hemicellulose component to a sugar solution containing pentose; and
a fermenter that produces, using the sugar solution obtained by the second enzymatic hydrolysis device, any one of alcohols, substitutes for petroleum, or amino acids by fermentation.

* * * * *